United States Patent
Tanaka et al.

(10) Patent No.: US 7,488,288 B2
(45) Date of Patent: Feb. 10, 2009

(54) ULTRASONIC ENDOSCOPE

(75) Inventors: Toshizumi Tanaka, Saitama (JP); Toshio Sakamoto, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 229 days.

(21) Appl. No.: 11/190,971

(22) Filed: Jul. 28, 2005

(65) Prior Publication Data

US 2006/0025691 A1 Feb. 2, 2006

(30) Foreign Application Priority Data

Jul. 29, 2004 (JP) ............................. 2004-221065
Nov. 5, 2004 (JP) ............................. 2004-321587

(51) Int. Cl.
*A61B 8/14* (2006.01)
(52) U.S. Cl. ................... 600/459; 600/437; 604/19; 604/20
(58) Field of Classification Search ......... 600/407–480; 604/19, 20
See application file for complete search history.

(56) References Cited

U.S. PATENT DOCUMENTS

| | | | | |
|---|---|---|---|---|
| 4,587,972 | A * | 5/1986 | Morantte, Jr. | 600/439 |
| 4,757,819 | A * | 7/1988 | Yokoi et al. | 600/156 |
| 5,109,861 | A * | 5/1992 | Walinsky et al. | 600/463 |
| 5,368,037 | A | 11/1994 | Eberle et al. | |
| 5,375,602 | A | 12/1994 | Lancee et al. | |
| 5,634,466 | A * | 6/1997 | Gruner | 600/459 |
| 6,059,731 | A * | 5/2000 | Seward et al. | 600/459 |
| 6,210,337 | B1 * | 4/2001 | Dunham et al. | 600/462 |
| 6,461,304 | B1 * | 10/2002 | Tanaka et al. | 600/462 |
| 6,592,526 | B1 * | 7/2003 | Lenker | 600/463 |
| 7,037,269 | B2 * | 5/2006 | Nix et al. | 600/459 |
| 2002/0022833 | A1 * | 2/2002 | Maguire et al. | 606/27 |
| 2002/0058873 | A1 * | 5/2002 | Seward et al. | 600/466 |

(Continued)

FOREIGN PATENT DOCUMENTS

JP 2001-314403 11/2001

OTHER PUBLICATIONS

U.S. Appl. No. 11/172,849, filed Jul. 05, 2005, Tanaka et al.

(Continued)

*Primary Examiner*—Brian L. Casler
*Assistant Examiner*—Nasir Shahrestani
(74) *Attorney, Agent, or Firm*—Oblon, Spivak, McClelland, Maier & Neustadt, P.C.

(57) ABSTRACT

An ultrasonic endoscope comprising an insertion portion comprising a distal hard portion which has: an endoscopic observation unit; and an ultrasonic observation unit fitted on an outer circumferential section of the endoscopic observation unit, wherein: the ultrasonic observation unit comprises: an ultrasonic transducer array having ultrasonic transducers, and a backing layer cylindrically formed on an inner circumferential surface of the ultrasonic transducer array; and a flexible circuit board on which formed are first terminals each connected to an electrode of a respective one of the ultrasonic transducers, second terminals to which cables are respectively connected, and wiring patterns respectively formed between the first and second terminals, wherein the flexible circuit board has a stepped structure having a large-diameter section on which the first terminals are formed and a small-diameter section on which the second terminals are formed, and an annular support section is formed on an inner circumferential side of the small-diameter section.

6 Claims, 16 Drawing Sheets

U.S. PATENT DOCUMENTS

2002/0087083 A1* 7/2002 Nix et al. .................... 600/459
2004/0068191 A1* 4/2004 Seward et al. ............... 600/466
2004/0097801 A1* 5/2004 Mesallum ................... 600/407

OTHER PUBLICATIONS

U.S. Appl. No. 11/190,971, filed Jul. 28, 2005, Tanaka et al.

* cited by examiner

ULTRASONIC ENDOSCOPE

BACKGROUND OF THE INVENTION

1. Field of the Invention

The present invention relates to an ultrasonic endoscope whose insertion portion includes a distal hard portion which has an endoscopic observation unit having an observation field of view forwardly of the endoscopic observation unit, and an electronic scanning type of ultrasonic observation unit having a circular or arcuate ultrasonic scanning plane perpendicular to the axis of the distal hard portion.

2. Description of the Related Art

A so-called electronic scanning type of ultrasonic endoscope has heretofore been widely used in which endoscopic observation means for observing a body cavity, an endoscopic mechanism including other means such as a treatment equipment insertion path through which to insert forceps or other treatment equipments, and ultrasonic observation means are fitted in a distal hard portion of an insertion portion and the ultrasonic observation means performs scanning by sequentially driving a multiplicity of ultrasonic transducers arranged in a predetermined direction in the ultrasonic observation means. For example, JP-A-2001-314403 describes a direct-view endoscope which has a field of view forwardly of a distal hard portion of its insertion portion as an observation field of view in the endoscopic observation means and in which the ultrasonic observation means has an ultrasonic scanning plane in its radial direction, i.e., a circular ultrasonic scanning plane or an ultrasonic scanning plane which is arcuate in a predetermined angular range.

The ultrasonic endoscope described in JP-A-2001-314403 is inserted into a body cavity tube, for example, an upper gastrointestinal tract such as the esophagus or the small intestine, or a lower gastrointestinal tract such as the large intestine, and an area which appears forward in the insertion direction is observed by the endoscopic observation means. If an area of interest such as a lesion is detected, the ultrasonic observation means is positioned to face the area of interest so that information about body tissues in the area can be acquired.

In the above-described type of ultrasonic endoscope, the number of ultrasonic transducers constituting an ultrasonic transducer array is made several tens or more in terms of resolution. Cables are respectively connected to electrodes of the ultrasonic transducers, and the connection of the cables to the electrodes is generally provided via a flexible circuit board made of a resin film. In the JP-A-2001-314403, the flexible circuit board is divided into a plurality of flexible circuit boards, and each of these flexible circuit boars is extended to an intermediate position in the insertion portion and is connected to a respective one of the cables. The insertion portion has a structure in which an angle portion and a flexible portion are sequentially joined to the distal hard portion fitted with the endoscopic observation means and the ultrasonic observation means, and the connection between the flexible circuit boards and the cables is provided at a position inside the flexible portion extended from the angle portion. Proximal ends of the flexible circuit board to which the respective cables are connected are placed in a free state.

In this construction, when the ultrasonic observation means is to be incorporated into the insertion portion, the ultrasonic observation means is inserted into the insertion portion with the cable connected to the flexible circuit board in advance, and the proximal ends of the cables are inserted by being drawn from the proximal side of the insertion portion, until the ultrasonic transducer array is arranged at the distal end of the insertion portion. The flexible circuit board needs to have a certain degree of rigidity in order to ensure the stability of connection of the cables to the flexible circuit board, so that during insertion into the insertion portion, the flexible circuit board is inserted while its side edges are being caught on other members, and insertion operationality is degraded. In addition, if the cables are operated while being extremely strongly pulled, there is a risk that the cables are broken.

In addition, since the ultrasonic observation means and the endoscopic observation means are incorporated in the insertion portion, the inside of the insertion portion has a high filling factor. Since the angle portion is sharply bent by a bending operation, the end of the angle portion is brought to a free state, and the flexible circuit having a certain extent of rigidity is forcedly folded during the bending of the angle portion, and the end is forced against another member, for example, a light guide constituting the endoscopic observation means, and an edge of the end may break the light guide made of a very thin optical fiber or a cable connected to a solid-state image pickup device. Furthermore, a treatment equipment insertion tube or an air/water feed tube is buckled or damaged, and other problems occur.

In other words, in the case where the flexible circuit board is used when the cables are respectively connected to a multiplicity of ultrasonic transducers, if part of the flexible circuit board is placed into a free state, an edge or corner section of the flexible circuit board which is placed in a free state interferes with other members and compresses or damages these members not only during the incorporation of the insertion portion but also during the operation of the ultrasonic endoscope.

The invention has been made in view of the above-described problems, and an object of the invention is to ensure the fixability and stability of cables connected to an ultrasonic transducer array and makes it possible to facilitate incorporation of endoscopic observation means into an insertion portion.

An ultrasonic transducer array is generally made of an approximately cylindrical unit, and a backing layer is arranged in the inside of ultrasonic transducers, while an acoustic lens is fitted on the outside of the ultrasonic transducers. The acoustic lens serves to focus ultrasonic beams transmitted from the ultrasonic transducers, and beams in directions perpendicular to an ultrasonic-wave transmission plane are improved by the acoustic lens. The ultrasonic transducer array is integrated with the above-mentioned members and the like and is incorporated in the distal hard portion of the insertion portion, and each member constituting the endoscopic observation means and the like is inserted through the inside of the ultrasonic transducer array formed in a cylindrical shape in this manner, specifically, a tunnel-shaped path formed in the inside of the backing layer.

The insertion portion of the ultrasonic endoscope is inserted into the body of a subject for the purposes of various examinations and treatments, so that the diameter of the insertion portion need be made as thin as possible. If the accuracy of examination by the ultrasonic observation means is to be increased, it is necessary to increase the size of each of the ultrasonic transducers so as to increase the output power thereof. Accordingly, not only the thickness of each of the ultrasonic transducers increases, but also the thickness of the backing layer must be increased. The endoscopic mechanism is inserted in the tunnel-shaped path formed in the inside of the backing layer.

The endoscopic mechanism needs at least an illumination section and an observation section because the endoscopic mechanism is used to optically observe body cavities. There is also a case where other members such as a treatment equipment insertion channel and a cleaning-fluid supply tube for an observation window are provided in the endoscopic mechanism. In the observation section in particular, there is a case where an objective lens and a solid-state image pickup device as well as, if necessary, various filters and a prism for bending an optical path are provided. The treatment equipment insertion channel is constructed to allow forceps and other treatment equipments to be inserted through, and is desirably made of a thick tube in order to allow insertion of large-sized treatment equipments.

As described above, the ultrasonic endoscope has the problem that if any of the functions of the ultrasonic observation means or the endoscopic mechanism is to be improved, the insertion portion must be made thick as needed. The inside diameter of the backing layer in particular has an extremely large influence on the fitting of the endoscopic mechanism. An object of the invention is to make it possible to ensure a wide fitting space for the endoscopic mechanism by making as wide as possible the cross section of the tunnel-shaped path formed by the backing layer.

SUMMARY OF THE INVENTION

To achieve the above-described object, the invention provides an ultrasonic endoscope comprising an insertion portion comprising a distal hard portion which has: an endoscopic observation unit having at least an illumination section and an observation section at its distal end surface; and an electronic scanning type of ultrasonic observation unit fitted on an outer circumferential section of the endoscopic observation unit, wherein: the ultrasonic observation unit comprises:

an ultrasonic transducer array having a plurality of ultrasonic transducers arranged cylindrically or circularly, and a backing layer cylindrically formed on an inner circumferential surface of the ultrasonic transducer array; and a flexible circuit board arranged between the ultrasonic transducer array and the backing layer, on which formed are a plurality of first terminals each connected to an electrode of a respective one of the ultrasonic transducers, a plurality of second terminals to which cables are respectively connected, and wiring patterns respectively formed between the first terminals and the second terminals, wherein the flexible circuit board has a stepped structure having a large-diameter section on which the first terminals are formed on an external surface side and a small-diameter section on which the second terminals are formed on an external surface side, and an annular support section is formed on an inner circumferential side of the small-diameter section.

The multiplicity of ultrasonic transducers which constitute the ultrasonic transducer array and the respective cables are electrically connected via the flexible circuit board, and the flexible circuit board is fitted on a support member. In this manner, the flexible circuit board is fitted on the support member so that the entire flexible circuit board is fixed, but an edge or a corner section does not project. However, if the connection sections between the flexible circuit board and the ultrasonic transducers are straightforward extended and connected to the cable, the outside diameter of the connection section of the cable becomes large. For this reason, the flexible circuit board is formed as a stepped structure, and the large-diameter section of the stepped structure is connected to the ultrasonic transducers and the small-diameter section of the stepped structure is connected to the cable, so that the diameter of the connection section between the flexible circuit board and the cables can be restrained.

The backing layer is provided on the inner circumferential side of the ultrasonic transducer array, and the thickness dimension of the backing layer is desirably as thick as possible. The support member which supports the small-diameter section of the flexible circuit board may be made of an independent member, but the backing layer itself can be made to function as the support member. In this case, the backing layer is projected by a predetermined length from an end section of the ultrasonic transducer array toward a proximal side of the distal hard portion and an outer circumferential surface of a section projected by the predetermined length is reduced in diameter to form a stepped structure, and the support section is formed by a reduced-diameter section of the stepped structure.

When the flexible circuit board is constructed as described above, the flexible circuit board has the stepped structure, so that folded sections are formed at two locations, i.e., the transition section from the large-diameter section to the stepped section and the transition section from the stepped section to the small-diameter section. The flexible circuit board may be formed in a stepped cylindrical shape in advance, but in this case, terminal sections and wirings are difficult to form on the flexible circuit board by printing means. For this reason, in pattern formation by printing, it is advantageous to construct the flexible circuit board from one planar resin film.

In the case where the flexible circuit board is formed of a planar resin film, the flexible circuit board needs to be folded at two locations, and each folding angle is generally 90°. Since the large-diameter section of the flexible circuit board is generally cylindrical, the large-diameter section is made of a continuous section, but cuts must be formed in the area between the transition section to the stepped section and an end of the small-diameter section at at least a predetermined pitch. However, if the cuts are only formed, the flexible circuit board will partially overlap in the small-diameter section. For this reason, the flexible circuit board is divided into a plurality of strips so that the flexible circuit board has the circumferential length of the small-diameter section. The strip-shaped discontinuous sections are formed at a predetermined pitch, and can be extended from the continuous section to the position of the transition section to the stepped section. In addition, the width dimension of each of the discontinuous sections can also be made uniform, and if necessary, may also be expanded from the distal side to the position of the transition section to the small-diameter section.

In other words, the flexible circuit board may comprise: a long section covering approximately the entire circumferential length of the large-diameter section; and a plurality of strip-shaped discontinuous sections having a first length approximately equal to a circumferential length of the small-diameter section, and each of the discontinuous sections has a second length extending from: a transition section from the long section to the stepped section; to an end section of the support section.

Folds are formed at two locations in the discontinuous sections, and each of these folds needs to be perpendicular and have a sharp folded shape in which wrinkles or irregularities are not formed as a whole or in part. If a folded section partially separates from the backing layer, not only the strength of fixation of the flexible circuit board to the backing layer is decreased, but also a defective connection to the ultrasonic transducers occurs or excessive external force acts on and causes damage to the ultrasonic transducers. To cope with this problem, each of the discontinuous sections of the flexible circuit board is constructed so that, for example, either a plurality of small holes or a plurality of cuts are formed along folding lines in the transition section from the large-diameter section to the stepped section and the transition section from the stepped section to the small-diameter section, thereby forming a sharply folded shape.

According to the above-described construction, since the cables are fixed to the flexible circuit board fixed to the support member, cable connection work can be easily performed, and the cables can be firmly fixed with stability ensured. Accordingly, it is possible to smoothly and easily perform the work of incorporating the ultrasonic observation means into the insertion portion, whereby it is possible to achieve the advantage of preventing the flexible circuit board or the like from compressing or damaging other members during operation.

According to the invention, there may be provided an ultrasonic endoscope, wherein an endoscopic mechanism is inserted in an inside of a tunnel-shaped path which is formed in an inside of the backing layer, the endoscopic mechanism comprising: the endoscopic observation unit; and other sections including a treatment equipment insertion channel, a filler which is the same as or close to the backing layer in acoustic impedance is charged in a spatial area which is produced in a section where the endoscopic mechanism is arranged in the inside of the backing layer.

The filler may comprise the same material as the backing layer and a solid-state image pickup device is provided in the observation section, at least part of the solid-state image pickup device being embedded in an inside of the filler.

Accordingly, since the filler can serve a function similar to the backing layer, it is possible to reduce the thickness of the backing layer which constitutes the ultrasonic observation means, and it is possible to achieve advantages such as widening the fitting space for the endoscopic mechanism by the corresponding amount.

DETAILED DESCRIPTION OF THE INVENTION

Figure 1:
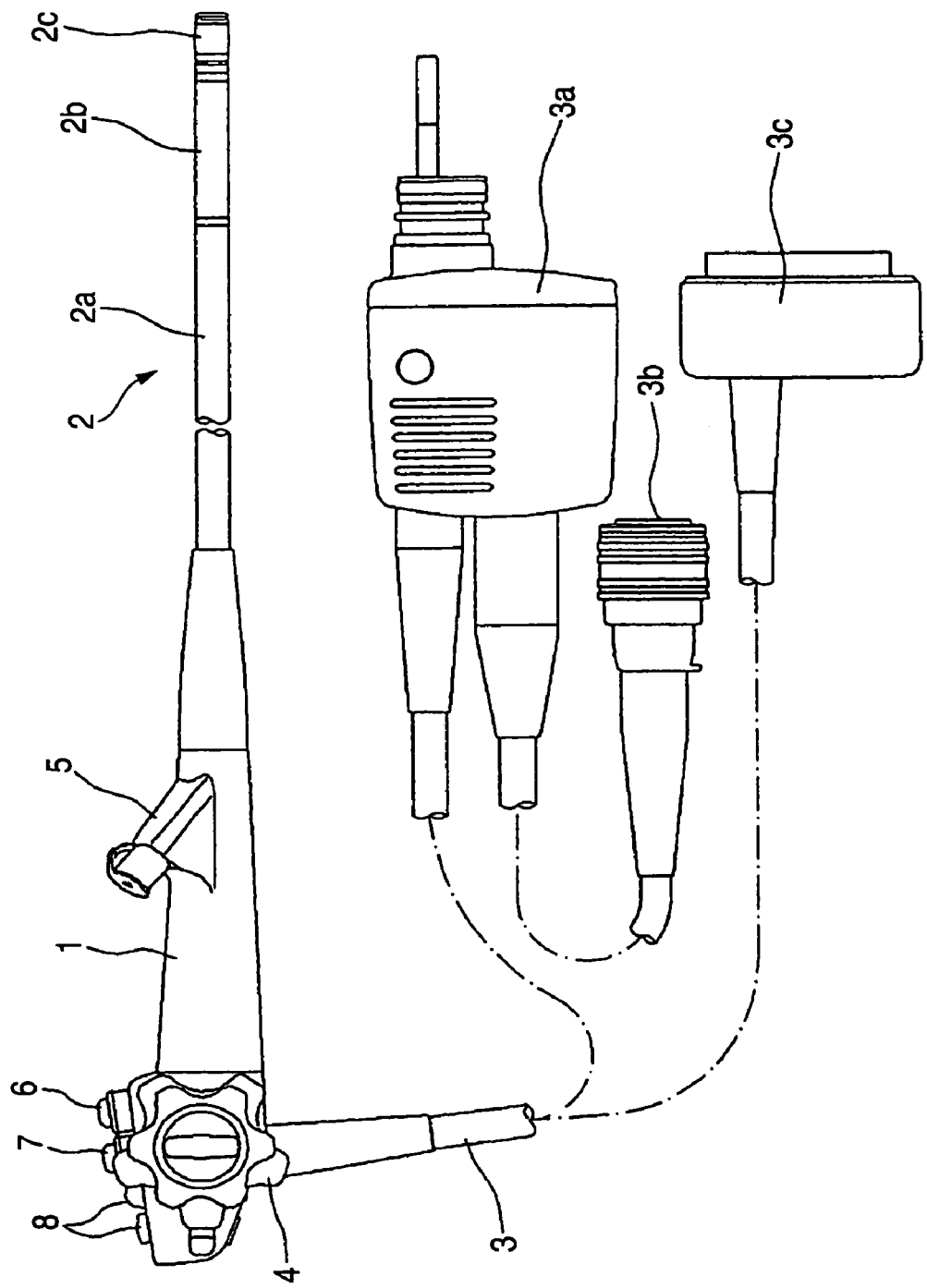
FIG. 1 is a general construction diagram showing an ultrasonic endoscope according to one preferred embodiment of the invention.

A preferred embodiment of the invention will be described below in detail with reference to the accompanying drawings. As shown in FIG. 1, an ultrasonic endoscope is generally made of a main control portion 1, an insertion portion 2, and a universal cord 3. A light source device, a video signal processing device and an ultrasonic observation device are connected to the ultrasonic endoscope so as to constitute the entire system. The universal cord 3 is extended from the main control portion 1 and is divided at a halfway position into branches which are respectively equipped with a connector 3a removably connected to the light source device, a connector 3b removably connected to the video signal processing device, and a connector 3c removably connected to the ultrasonic observation device.

The main control portion 1 can be grasped in one hand by an operator or the like, and is provided with angle operation means 4 and a treatment equipment guiding portion 5 and is also equipped with an air/water feed button 6, an suction button 7 and other switches 8.

The insertion portion 2 is a cord-like member joined to the main control portion 1 and having a predetermined length, and is inserted into the body of a subject and the like. In this insertion portion 2, nearly all length extending from a position where the insertion portion 2 is joined to the main control portion 1 is formed as a flexible portion 2a having a structure arbitrarily bendable along an insertion path in a body cavity and the like. An angle portion 2b is joined to the distal end of the flexible portion 2a, and a distal hard portion 2c is joined to the angle portion 2b. The angle portion 2b can be bent upwardly, downwardly, leftwardly and rightwardly by remote operation in order to direct the distal hard portion 2c in a desired direction. Accordingly, the main control portion 1 is provided with the angle operation means 4 so that the angle portion 2b can be bent by the operation of the operator so as to direct the distal hard portion 2c in a desired direction.

Figure 2:
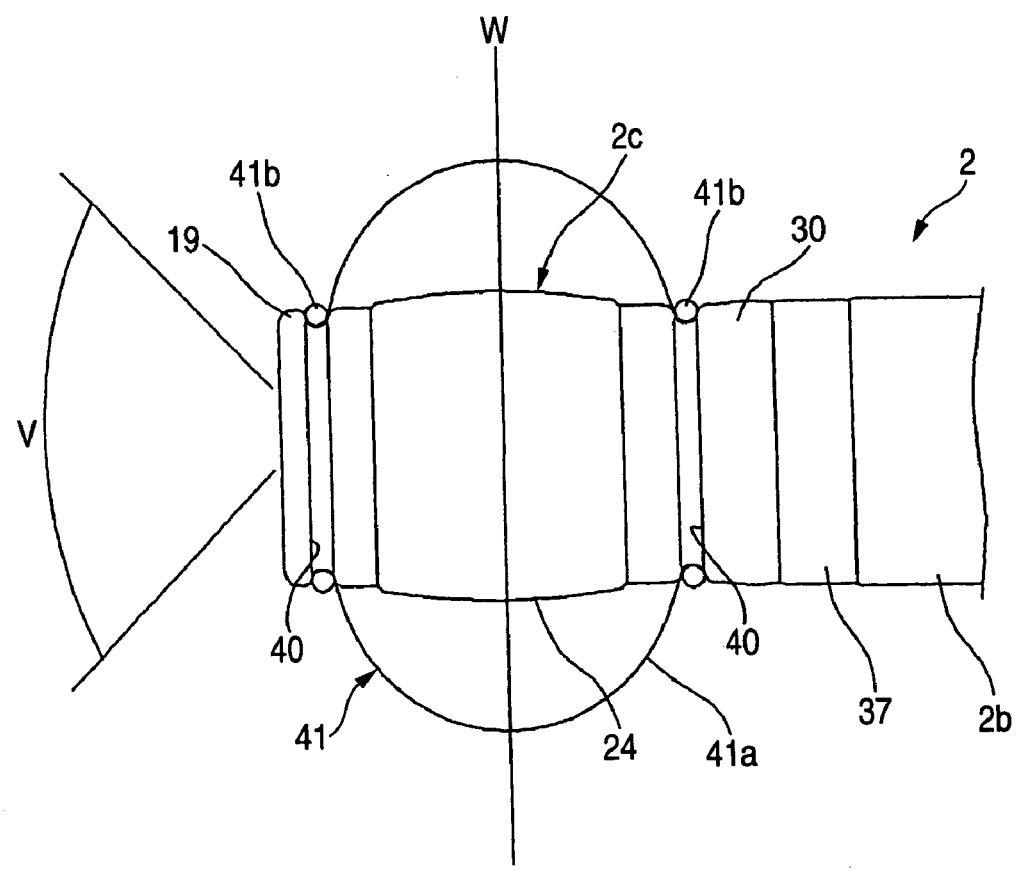
FIG. 2 is a schematic view of an external appearance of a distal end of an insertion portion of the ultrasonic endoscope according to the preferred embodiment of the invention.
Figure 3:
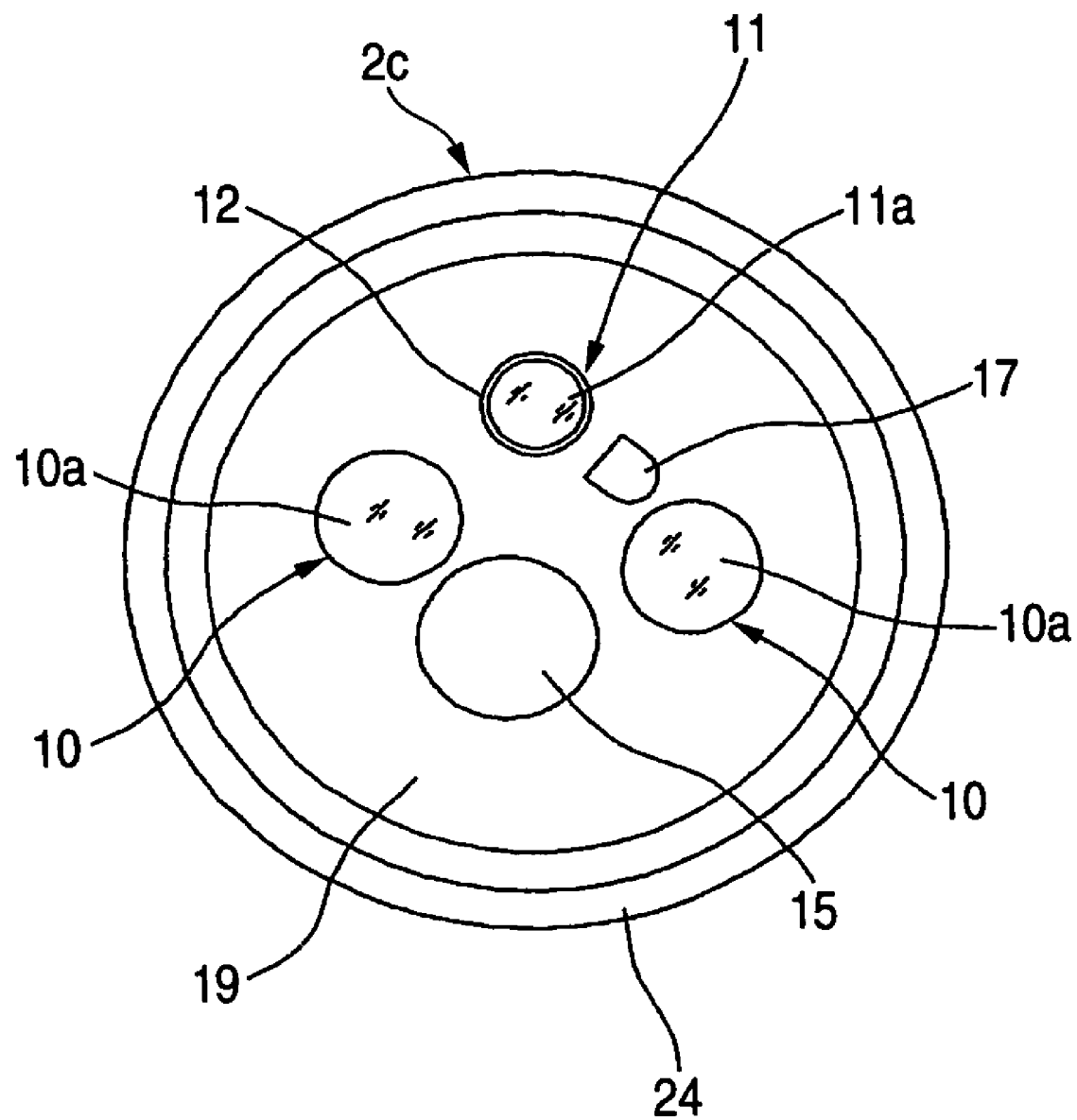
FIG. 3 is a schematic view showing a distal end surface of a distal hard portion of the ultrasonic endoscope according to the preferred embodiment of the invention.

FIG. 2 shows a distal end of the insertion portion 2, and FIG. 3 shows the construction of a distal end surface of the distal hard portion 2c. As is apparent from FIGS. 2 and 3, the distal hard portion 2c is provided with an endoscopic observation unit which has a field of view with a predetermined viewing angle V in the extension direction of the axis of the distal hard portion 2c, i.e., forwardly of the distal hard portion 2c, and an electronic radial scan type of ultrasonic observation unit having a circular or arcuate ultrasonic scanning plane W at a position displaced toward a proximal side from the field of view of the endoscopic observation unit.

Figure 4:
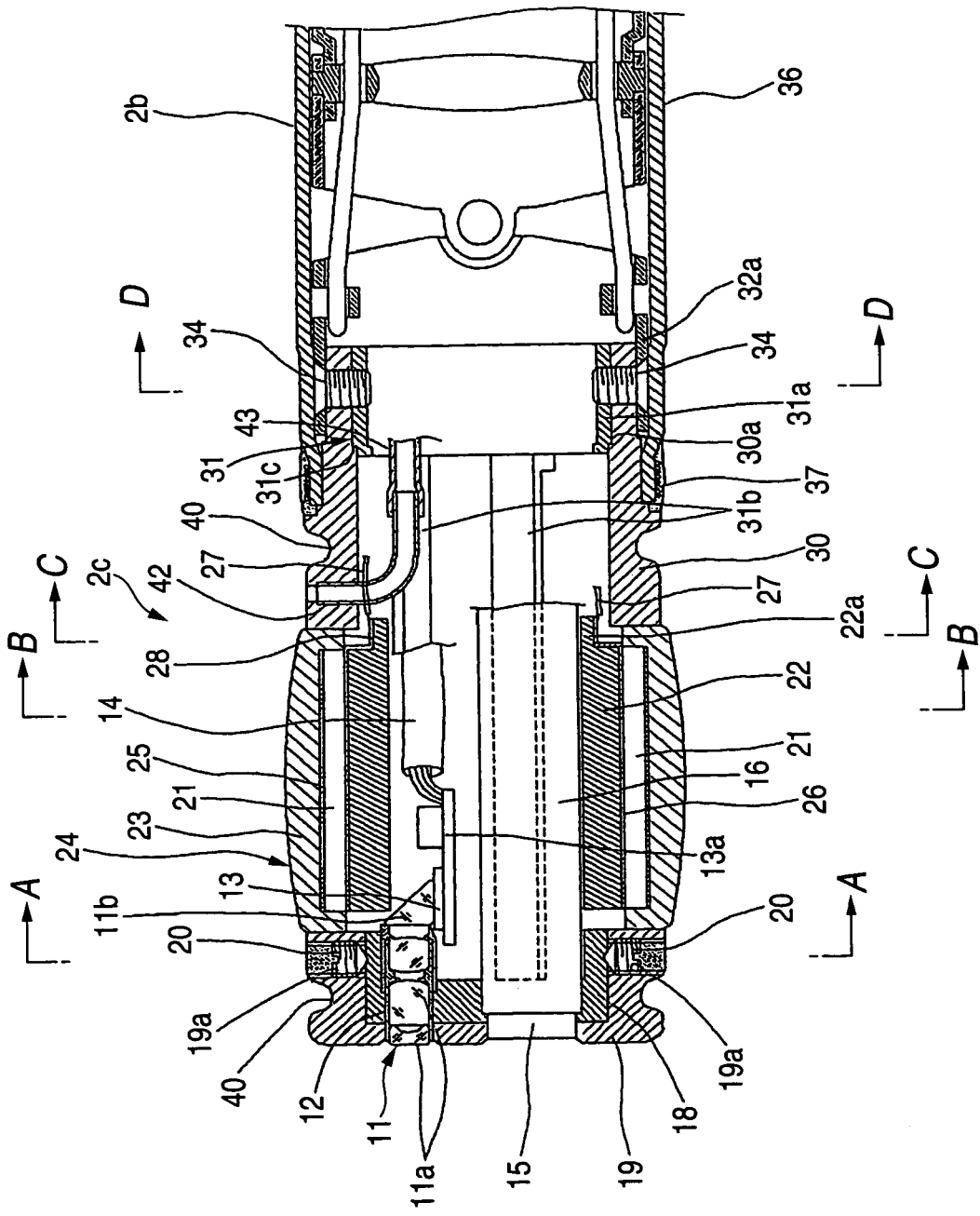
FIG. 4 is a vertical cross-sectional view of the distal hard portion.

FIG. 4 shows a cross section of the distal end of the insertion portion 2. As is apparent from FIGS. 3 and 4, the endoscopic observation unit is made of illumination sections 10 and an observation section 11, and the respective illumination sections 10 are arranged at opposite positions between which the observation section 11 is positioned. Each of the illumination sections 10 is made of an illumination lens 10*a* and a light guide 10*b* (refer to FIGS. 5 to 8) which face the distal end surface of the distal hard portion 2*c*. The light guide 10*b* is made of a bundle of a number of extrafine optical fibers, and is extended from the connector 3*a* of the universal cord 3 to the distal hard portion 2*c* of the insertion portion 2 so that its illumination light emission end faces a position which opposes the illumination lens 10*a*. On the other hand, the observation section 11 is made of an objective lens 11*a* and a prism 11*b* which bends an optical path entering from the objective lens 11*a* at 90°, and the objective lens 11*a* is provided in a lens barrel 12 and the prism 11*b* is provided in the state of being fixed to the lens barrel 12. A solid-state image pickup device 13 is joined to the prism 11*b*, and a predetermined number of signal lines are connected to a circuit board 13*a* of the solid-state image pickup device 13. These signal lines are bundled and extended to the connector 3*b* of the universal cord 3.

The distal end surface of the distal hard portion 2*c* of the insertion portion 2 is provided with a treatment equipment lead-out opening 15 through which to pass forceps and other treatment equipments, and the treatment equipment lead-out opening 15 is fitted with a connection pipe 16 to which a treatment equipment insertion tube extending from a treatment equipment guiding portion 5 provided in the main control portion 1 is connected. The treatment equipment insertion tube is constructed to meet a suction path in the inside of the main control portion 1. Furthermore, the distal hard portion 2*c* is fitted with a nozzle 17 for cleaning the distal end surface of the objective lens 11*a* in the observation section 11 when it is contaminated by a body fluid. A cleaning-fluid supply tube 9 (see FIGS. 5 to 8) to be operated through the air/water feed button 6 is connected to the nozzle 17. Accordingly, these members also function as an endoscopic mechanism constituting an endoscope together with the endoscopic observation unit.

Figure 5:
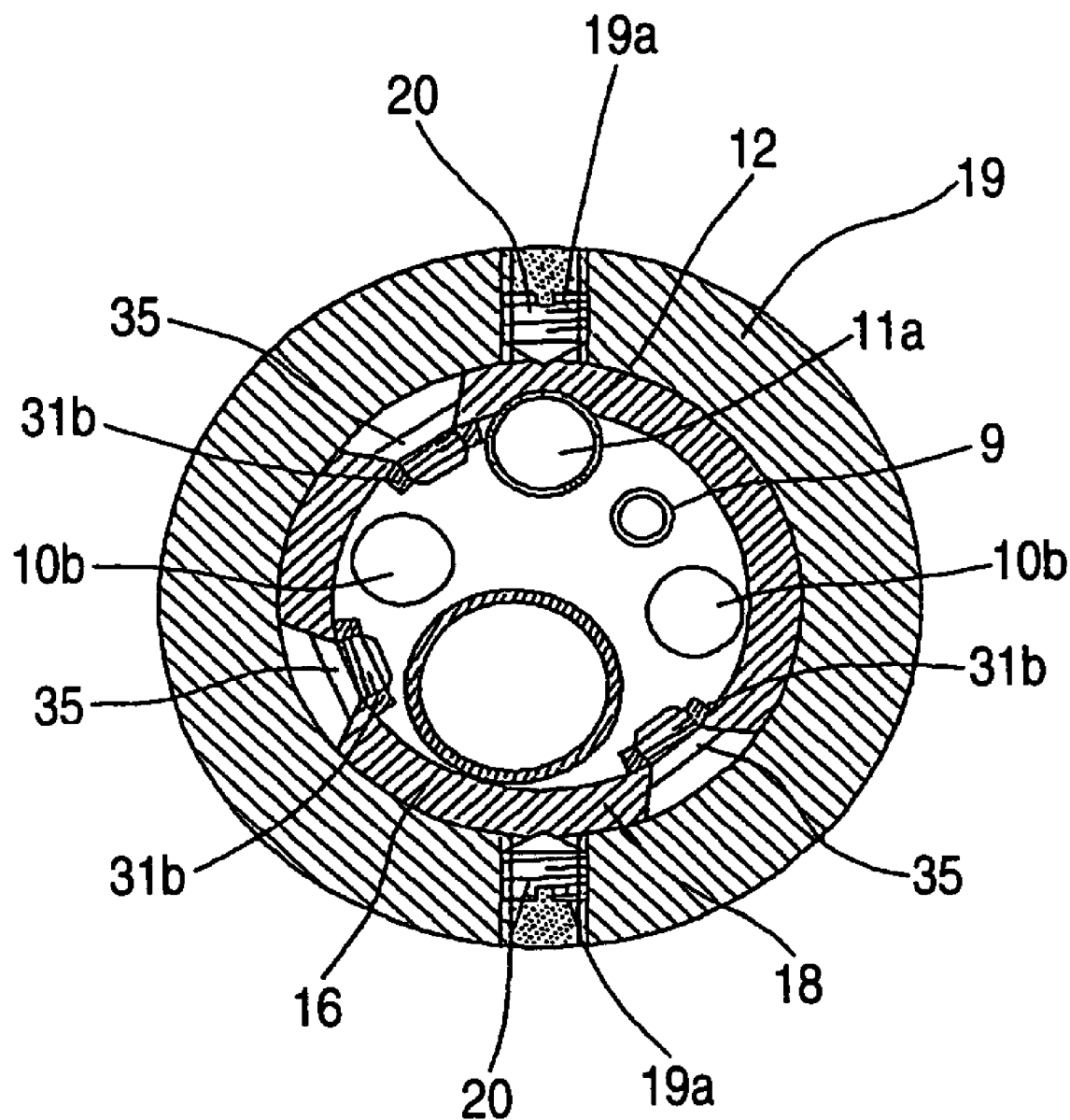
FIG. 5 is a cross-sectional view taken along line A-A of FIG. 4.
Figure 6:
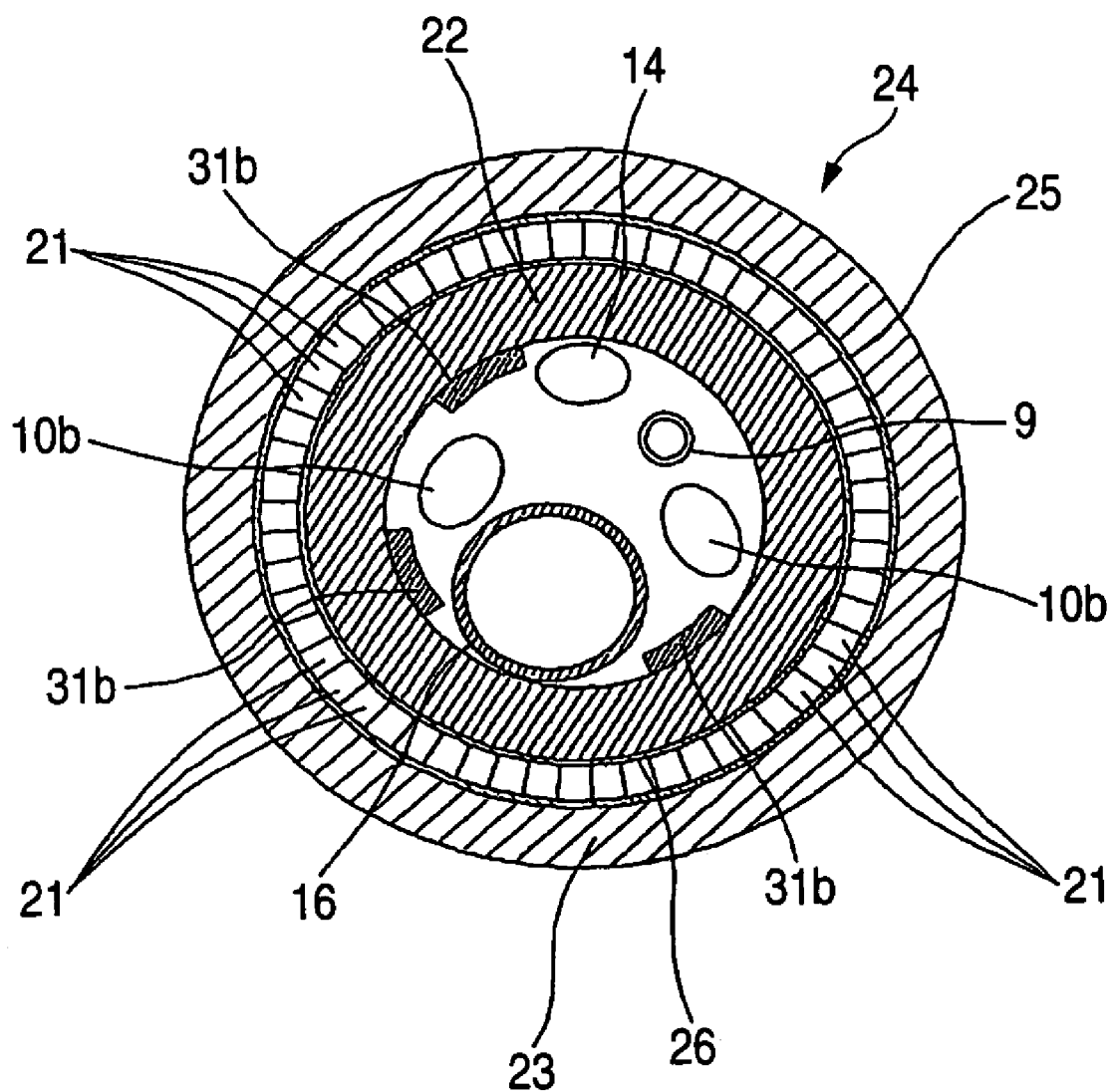
FIG. 6 is a cross-sectional view taken along line B-B of FIG. 4.

The endoscopic observation unit is constructed in the above-described manner, and the distal ends of the respective members constituting the endoscopic observation unit are fixedly held by an endoscope fitting member 18. The endoscope fitting member 18 is made of a metallic material, such as stainless steel, in which are formed a plurality of through-holes through which to insert the respective members constituting the above-mentioned endoscopic observation unit. A distal cap 19 is fitted on the endoscope fitting member 18 so as to prevent the endoscope fitting member 18 made of the metallic material from being exposed to the outside. The endoscope fitting member 18 and the distal cap 19 constitute a distal end block. As shown in FIG. 5, two screw holes 19*a* are formed to extend through the distal cap 19 in the thickness direction thereof, and set screws 20 are respectively screwed into the screw holes 19*a* so that the distal ends of the set screws 20 are pressed against the endoscope fitting member 18 and the abutment surfaces between the endoscope fitting member 18 and the distal cap 19 are joined together. In this manner, the distal end block made of the endoscope fitting member 18 and the distal cap 19 is integrated.

The ultrasonic observation unit having a radial scanning plane is provided in the distal hard portion 2*c* at a proximal position of the distal cap 19. As is apparent from FIG. 6, the ultrasonic observation unit is made of a ultrasonic transducer array in which a multiplicity of ultrasonic transducers 21 are arranged in the circumferential direction, and the ultrasonic transducers 21 are arranged in a circumferential or arcuate form (for example, approximately 270°) so as to perform electronic scanning. A backing layer 22 is fitted on the inner circumferential side of the ultrasonic transducers 21 arranged in this manner. The multiplicity of ultrasonic transducers 21 are fixed to the backing layer 22 by means of adhesion or the like. An acoustic lens 23 is fitted on the outer circumferential face of the ultrasonic transducers 21, thereby constituting an ultrasonic wave transmission/reception unit 24 having a generally cylindrical shape.

Figure 7:
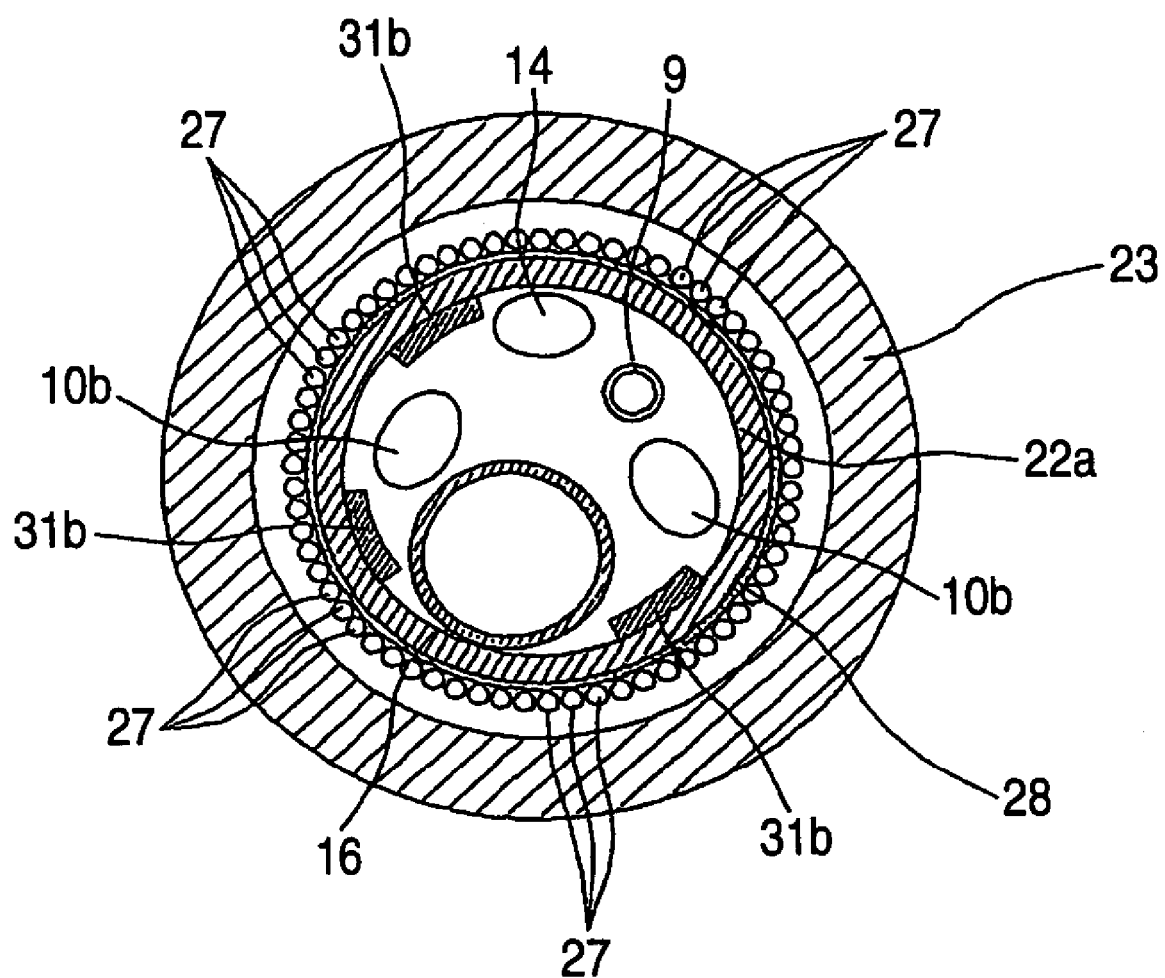
FIG. 7 is a cross-sectional view taken along line C-C of FIG. 4.
Figure 8:
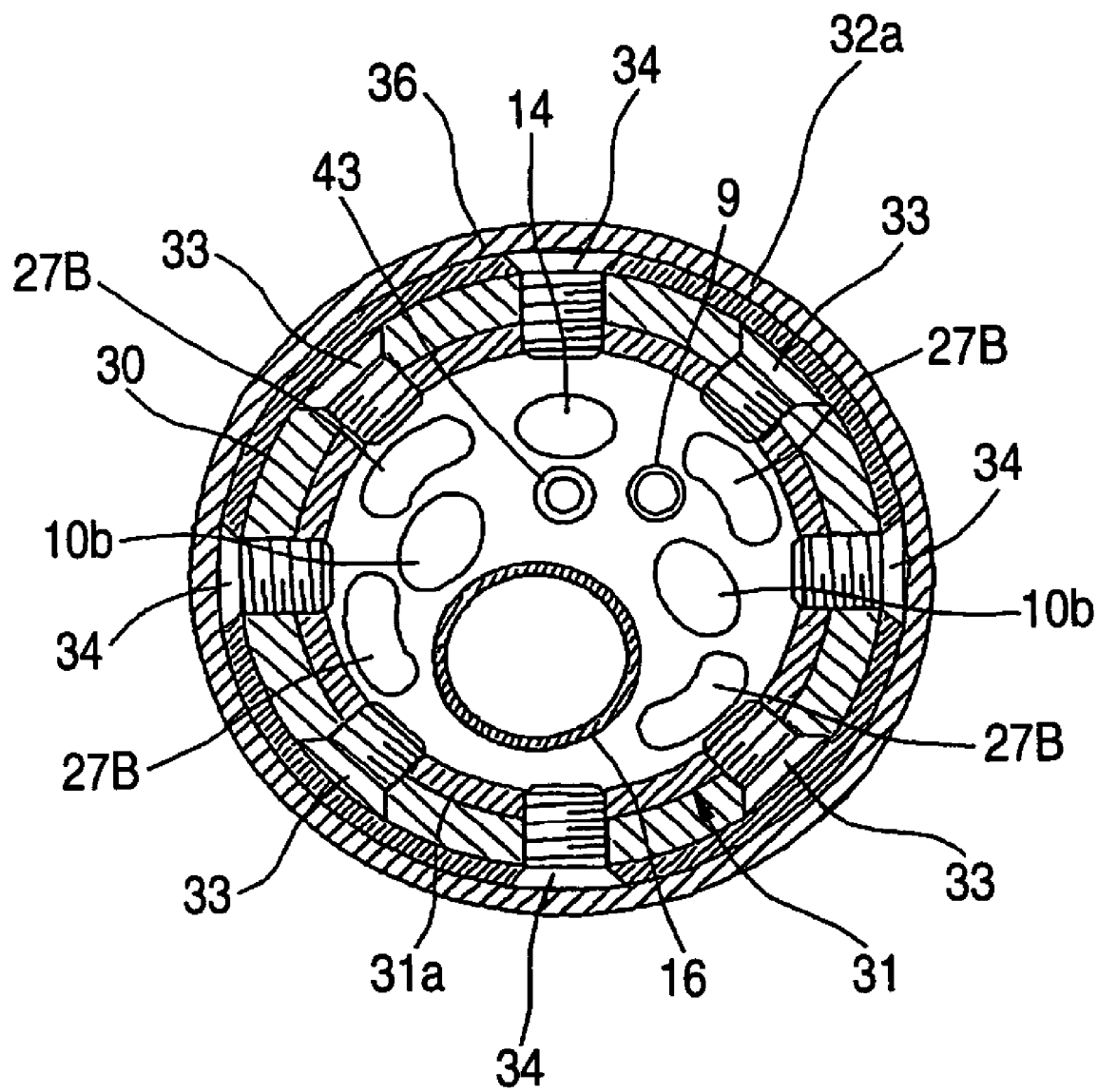
FIG. 8 is a cross-sectional view taken along line D-D of FIG. 4.

Each of the ultrasonic transducers 21 has two electrode 25 and 26, and the electrode 25 is a common electrode common to all (or each predetermined number of) the ultrasonic transducers 21. The electrodes 26 are individually provided for the respective ultrasonic transducers 21. The individual electrodes 26 of the ultrasonic transducers 21 are electrically connected to wiring patterns formed on a flexible circuit board 28 as will be described later. As shown in FIG. 7, a predetermined number of cables 27 are respectively connected to the individual electrodes 26 via the flexible circuit board 28. In principle, the flexible circuit board 28 may be connected to the cables 25 by one cable, and although not shown, the one cable is connected on the distal side of the ultrasonic transducers 21.

As described above, the ultrasonic wave transmission/reception unit 24 has an approximately cylindrical shape, and its inner circumferential surface forms a tunnel-shaped path. The members constituting the endoscopic observation unit are inserted through the tunnel-shaped path formed by the ultrasonic wave transmission/reception unit 24 and are positioned on the distal side from the ultrasonic wave transmission/reception unit 24, and are fixed to the endoscope fitting member 18 covered with the distal cap 19. A distal end of the ultrasonic wave transmission/reception unit 24 abuts on an end surface of the distal cap 19, while a proximal side of the ultrasonic wave transmission/reception unit 24 abuts on an end surface of a joining member 30. The joining member 30 constitutes a joining section between the angle portion 2*b* and the distal hard portion 2*c*.

Furthermore, a bridge member 31 is provided in the inside of the joining member 30, so that a distal ring 32*a* of angle rings which constitute the structure of the angle portion 2*b* is joined to the connection member 30 and the bridge member 31. Namely, as is apparent from FIG. 8, the joining member 30 and the bridge member 31 are joined together by a plurality of screws 33, and the distal ring 32*a* is joined to the joining member 30 and the bridge member 31 by a plurality of screws 34.

Figure 9:
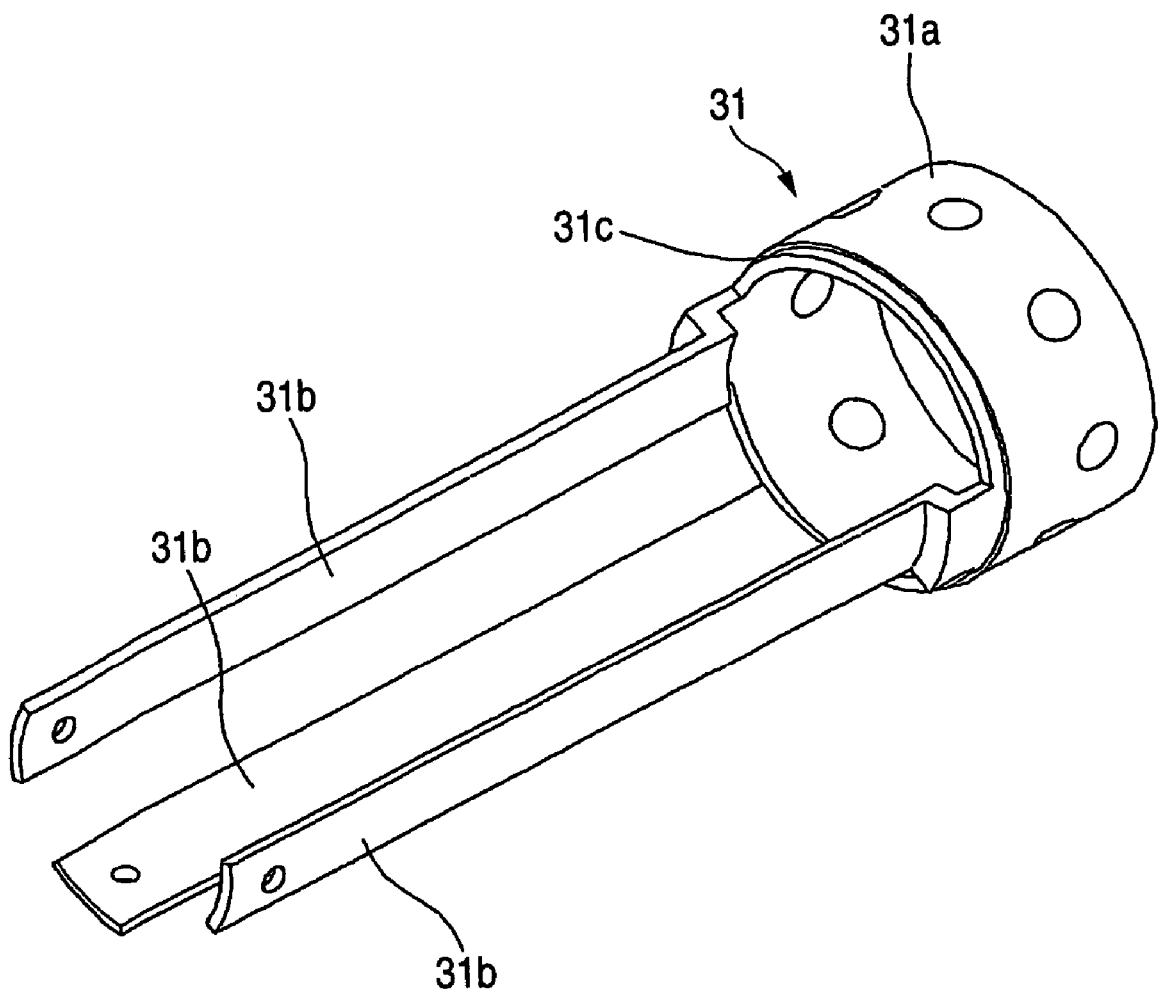
FIG. 9 is a perspective view of an external appearance of a bridge member of the ultrasonic endoscope according to the preferred embodiment of the invention.

The bridge member 31 serves the function of joining the joining member 30 arranged on the most proximal side of the distal hard portion 2*c* to the distal ring 32*a* arranged at the distal position of the angle portion 2*b*, the function of restricting the position of the ultrasonic wave transmission/reception unit 24 comprising the ultrasonic transducer array in directions perpendicular to the axis of the distal hard portion 2*c*, and a joining function for a joining structure between the endoscope fitting member 18 and the distal cap 19. Accordingly, the bridge member 31 is formed of a metal such as stainless steel because the bridge member 31 is a member which needs to have a high strength and is not exposed to the outside. As shown in FIG. 9, the bridge member 31 has a tubular section 31*a* joined to the joining member 30 and the distal ring 32*a* of the angle portion 2*b* by the screws 33 and 34, and a plurality of (in the present embodiment, three) joining arms 31*b* are extended from the tubular section 31*a* toward the distal end.

The ultrasonic wave transmission/reception unit 24 is positioned in directions perpendicular to the axis of the joining arms 31*b* by being fitted into the joining arms 31*b*, and the entire distal hard portion 2c is fixed in an assembled state by the distal ends of the respective arms 31b and the endoscope fitting member 18 being joined by screws 35. A step 31c is formed around the outer circumferential surface of the tubular section 31a of the bridge member 31, and the tubular section 31a extending from the step 31c toward the proximal side is larger in diameter than the step 31c. A step 30a is formed around the inner circumferential surface of the joining member 30, and the inner circumferential surface extending from the step 30a is larger in diameter than the step 30a. The ultrasonic wave transmission/reception unit 24 is clamped between the distal cap 19 and the joining member 30 by the steps 30a and 31c being joined together. When the opposite end surfaces of the ultrasonic wave transmission/reception unit 24 are respectively bonded to the proximal surface of the distal cap 19 and the distal surface of the joining member 30, the ultrasonic wave transmission/reception unit 24 is positioned in the direction of the axis thereof and is rotationally stopped, whereby the ultrasonic wave transmission/reception unit 24 is fixedly held at a predetermined position. A sheath layer 36 of the angle portion 2b is extended to a proximal outer circumferential section of the joining member 30, and the distal end of the sheath layer 36 is fixed to the joining member 30 of the distal hard portion 2c by a fixation mechanism 37 made of a bobbin and an adhesive.

Figure 10:
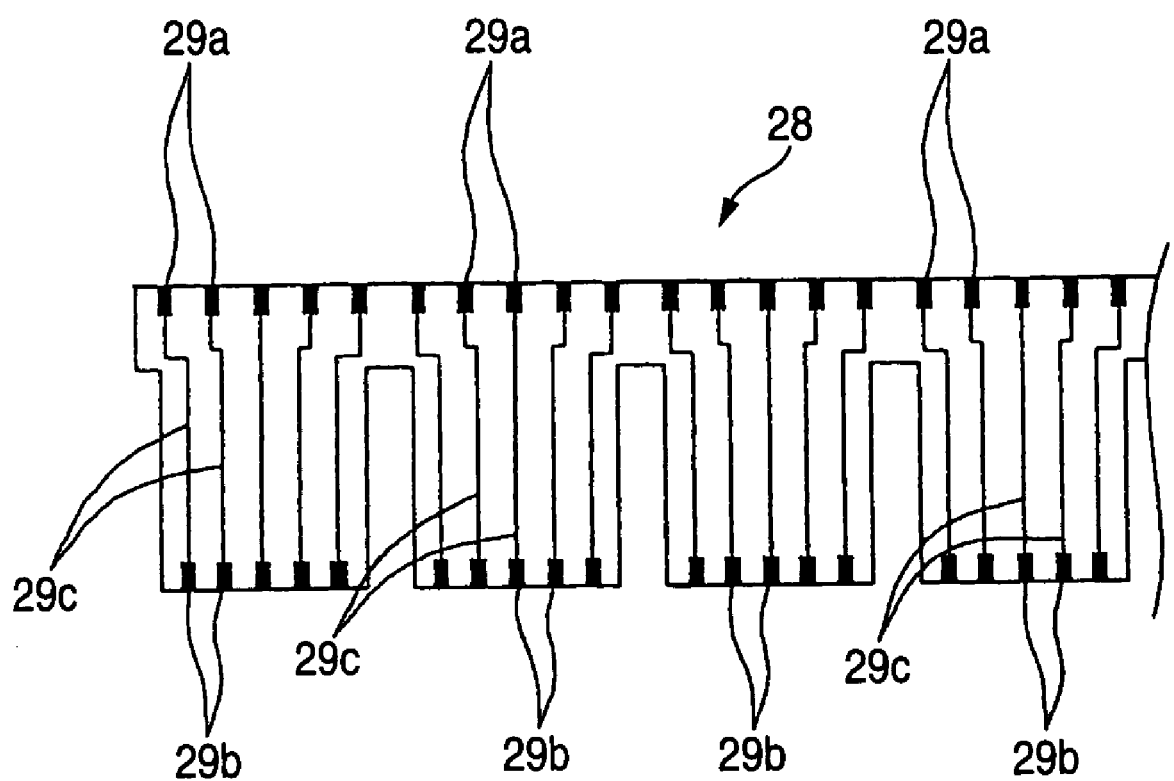
FIG. 10 is a developed view of an essential section of a flexible circuit board of the ultrasonic endoscope according to the preferred embodiment of the invention.
Figure 11:
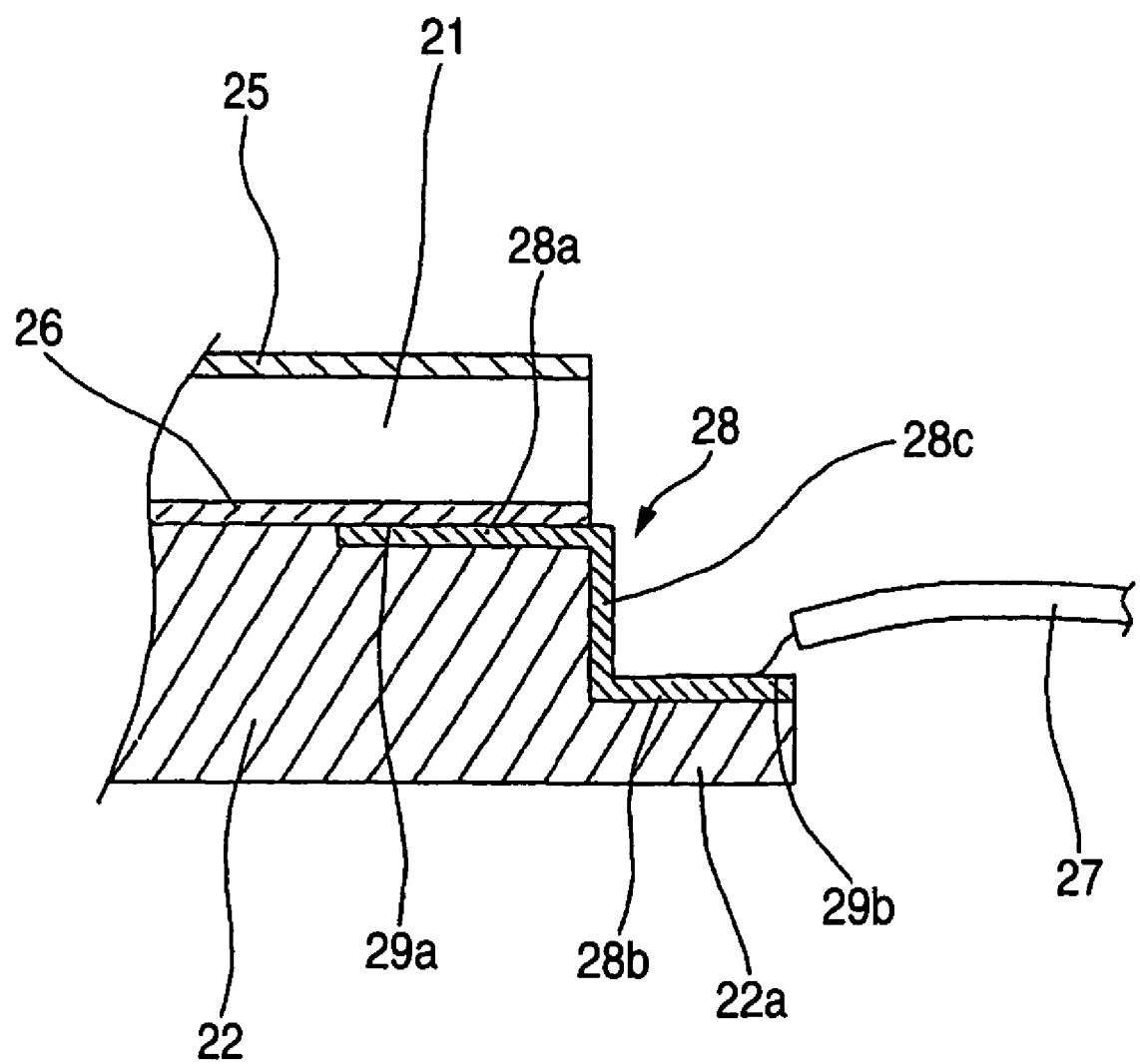
FIG. 11 is an enlarged cross-sectional view showing joining sections between the flexible circuit board and an ultrasonic transducer as well as a backing layer.

As described above, the multiplicity of ultrasonic transducers 21 and the cables 27 are respectively electrically connected to each other via the flexible circuit board 28. Accordingly, the flexible circuit board 28 is inserted between the ultrasonic transducers 21 and the cables 27 in a clamped manner. As shown in FIG. 10 in a developed form, the flexible circuit board 28 has required wiring patterns formed as by printing. Each of the wiring patterns is made of a first terminal section 29a electrically connected to the corresponding one of the individual electrodes of the ultrasonic transducers 21, a second terminal section 29b electrically connected to the corresponding one of the cables 27 as by soldering, and a wiring 29c interconnecting the first and second terminal sections 29a and 29b. The flexible circuit board 28 is incorporated in the distal hard portion 2c in a generally cylindrical shape, and as shown in FIG. 11 as well, a large-diameter section 28a is provided on a side where the ultrasonic transducers 21 which constitute an ultrasonic transducer array arranged in an annular shape are joined to the backing layer 22 (i.e., on a side where the first terminal sections 29a are formed), and a small-diameter section 28b is provided on a side to which the cables 27 are connected (i.e., on a side where the second terminal sections 29b are formed), and a vertical section 28c is provided as a step between the large-diameter section 28a and the small-diameter section 28b.

As described above, the flexible circuit board 28 is formed in a stepped cylindrical shape, and is stuck to the backing layer 22. The ultrasonic transducers 21 are annularly arranged around the outer circumferential surface of the backing layer 22, and the first terminal sections 29a on the flexible circuit board 28 are respectively electrically connected to the individual electrodes 26 formed on the ultrasonic transducers 21. Accordingly, the large-diameter section 28a of the flexible circuit board 28 has approximately the same cylindrical shape as the backing layer 22, and is fitted in a clamped manner between the electrodes 26 of the ultrasonic transducers 21 and the backing layer 22.

As is apparent from FIG. 4, the inner circumferential surface of the ultrasonic transducers 21 is positioned on the outside of the outer circumferential surface, so that if the flexible circuit board 28 is extended straightforward toward the proximal side, the flexible circuit board 28 will interfere with the joining member 30. This is why the small-diameter section 28b is provided on the proximal side of the flexible circuit board 28 having a cylindrical shape. The second terminal sections 29b are formed on the small-diameter section 28b, and the cables 27 are respectively electrically connected to the second terminal sections 29b as by soldering. The small-diameter section 28b is placed not in a free state but in abutment with a support member, and is fixed to the outer surface of the support member as by adhesion. The support member is formed by a small-diameter section 22a which is provided integrally with the backing layer 22 and has a diameter smaller than the diameter of the outer circumferential surface of the backing layer 22.

It can be considered that, in this construction, the support member formed by a member separate from the backing layer 22 is inserted into the inside of the tunnel-shaped path formed by the inside diameter of the backing layer 22. However, in this case, the thickness of the backing layer 22 is reduced, and the reflection action of ultrasonic waves occurs due to the difference in acoustic impedance between the backing layer 22 and the support member. For this reason, in order to increase the thickness of the backing layer 22, the backing layer 22 is extended toward the proximal side not for the purpose of a backing function but for the purpose of realizing the function of the support member which supports the small-diameter section 28b of the flexible circuit board 28. The extended section of the backing layer 22 is reduced in diameter and formed as the small-diameter section 22a, and the small-diameter section 28b of the flexible circuit board 28 is fixed to the small-diameter section 22a by adhesion. In addition, the stepped wall of the backing layer 22 and the vertical section 28c which is a transition section from the large-diameter section 28a of the flexible circuit board 28 to the flexible circuit board 28 are held in the state of being fixed to each other by adhesion.

As described previously, the multiplicity of cables 27 connected to the flexible circuit board 28 are positioned on the outer circumferential side of the small-diameter section 22a of the backing layer 22, and the cables 27 are connected to the flexible circuit board 28 and are led therefrom on a more outer circumferential side than the arrangement position of the bridge member 31. At the position shown in FIG. 8, i.e., at the position of the joining section between the distal hard portion 2c and the angle portion 2b, the cables 27 are inserted through the inside of the bridge member 31. Accordingly, the cables 27 are led so as to extend through the thickness direction of the bridge member 31. In this construction, the cables 27 are passed through a space formed by the divided joining arms 31b of the bridge member 31. The multiplicity of cables 27 are grouped into a plurality of bundles, for example, approximately four bundles, and cable bundles 27B obtained in this manner are deformably inserted from the angle portion 2b into the flexible portion 2a.

The members constituting the endoscopic observation unit are inserted into the inner circumferential section of the ultrasonic wave transmission/reception unit 24 which forms the tunnel-shaped path. Among the members, the two bundled light guides 10b and the video cable 14 are deformed into arbitrary cross-sectional shapes. The other inserted members are the connection pipe 16 which constitutes a treatment equipment insertion path, the cleaning-fluid supply tube 9, and a tube 43 for supplying an ultrasonic-wave transmission medium into a balloon 41 which will be described later. In addition, a flexible tube is joined to the connection pipe 16 which constitutes the treatment equipment insertion path, on the proximal side from the position shown in FIG. 8 or in the vicinity of the position shown in FIG. 8. Furthermore, as described previously, the cables 27 connected to the respective ultrasonic transducers 21 are grouped into bundles each having a predetermined number of cables, and the cables 27B are also passed through the tunnel-shaped path and extended into the angle portion 2b.

The ultrasonic transducers 21 which constitute the ultrasonic wave transmission/reception unit 24 transmit ultrasonic waves into the body, and the ultrasonic wave transmission/reception unit 24 receives echoes from cross sections of tissues in the body. In order to restrain the attenuation of ultrasonic waves transmitted and received in this manner, annular concave grooves 40 are respectively formed at front and rear positions between which the ultrasonic wave transmission/reception unit 24 is provided, i.e., around the respective outer peripheries of the distal cap 19 and the joining member 30, and as is apparent from FIG. 2, a balloon 41 to be swollen by injecting the ultrasonic-wave transmission medium thereinto is fitted between the annular concave grooves 40. The balloon 41 is made of a tubular flexible film 41a, and fixation rings 41b to be fixedly fitted on the respective annular concave grooves 40 are provided on the opposite ends of the flexible film 41a. The fixation rings 41b are fixedly fitted so that tightening forces act on the respective annular concave grooves 40. A charge/discharge path 42 for charging or discharging the ultrasonic-wave transmission medium into or from the joining member 30 is formed in the joining member 30, and a tube 43 is connected to the charge/discharge path 42.

In this construction, an image of a body cavity of a subject is displayed on a monitor for displaying endoscopic images by inserting the insertion portion 2 into the body cavity, irradiating illumination light onto the body cavity from the illumination sections 10 which constitute the endoscopic observation unit, forming an image of the body cavity onto the solid-state image pickup device 13 by the objective lens 11a provided in the observation section 11, acquiring a video signal of the body cavity from the solid-state image pickup device 13 and transmitting the video signal to the video signal processing device, and performing predetermined signal processing in the video signal processing device. Accordingly, the operator can perform endoscopy on the state of the body cavity by watching the monitor.

If an area of interest such as a lesion is discovered as the result of the endoscopy, the ultrasonic wave transmission/reception unit 24 which constitutes the ultrasonic observation unit is moved to a position facing the area of interest. Namely, when the insertion portion 2 is advanced by a predetermined distance, the ultrasonic wave transmission/reception unit 24 is located at the position facing the area of interest. Then, the ultrasonic-wave transmission medium is supplied into the balloon 41 to cause the flexible film 41a to swell into close contact with an inner wall of the body cavity. In this state, the ultrasonic transducers 21 arranged in the circumferential direction to constitute the ultrasonic wave transmission/reception unit 24 are sequentially actuated to transmit ultrasonic pulses into the body and receive echoes. The ultrasonic transducers 21 can also be actuated sequentially one by one, but each plurality of the ultrasonic transducers 21 is actuated with a predetermined time lag so as to effect electronic focusing, for example. An electronic scanning method for the ultrasonic transducers 21 arranged in multiplicity is well known, and the description of such a method is omitted herein.

The echo signals acquired by the respective ultrasonic transducers 21 which constitute the ultrasonic wave transmission/reception unit 24 are transmitted to the ultrasonic observation device, and in the ultrasonic observation device, the echo signals are subjected to signal processing, so that tomographic information about the states of body tissues including the area of interest is acquired. This ultrasonic tomographic image is displayed on the monitor attached to the ultrasonic observation device. Accordingly, the operator can make a diagnosis as to whether a lesion is contained in the tissues, and the like.

The members constituting the endoscopic observation unit, i.e., the light guides 10b, the video cable 14, the connection pipe 16 constituting the treatment equipment insertion path, the cleaning-fluid supply tube 9, the cable bundles 27B which are led from the ultrasonic wave transmission/reception unit 24 constituting the ultrasonic observation unit, and the tube 43 for supplying an ultrasonic-wave transmission medium into the balloon 41, are assembled by being inserted into the main control portion 1 from at least the insertion portion 2.

In assembly, the tube 43 connected to the joining member 30 and the cable bundles 27B connected to the ultrasonic wave transmission/reception unit 24 are inserted through a distal opening side of the angle portion 2b at the distal end thereof with the insertion portion 2 being separated from the main control portion 1, and the cable bundles 27B are inserted into the inside of the flexible portion 2a from the angle portion 2b. The tube 43 has flexibility and the cables 27 are grouped into bundles each having a predetermined number of cables, and the cable bundles 27B bundled in this manner can be easily led to the proximal side of the flexible portion 2a of the insertion portion 2. In addition, since the cable bundles 27B have flexibility in bending directions and are deformable in their bundled states, the cable bundles 27B can be extremely easily inserted into the insertion portion 2, and can also be smoothly inserted without being caught on angle rings or other members which constitute the angle portion 2b.

Then, the members constituting the endoscopic observation unit are incorporated into the endoscope fitting member 18, and the endoscope fitting member 18 is joined to the distal cap 19 by the screws 20, thereby forming an integrated distal block. In this state, the light guides 10b, the video cable 14, the connection pipe 16 and the cleaning-fluid supply tube 9 are sequentially inserted through the angle portion 2b and the flexible portion 2a from the tunnel-shaped path formed by the ultrasonic wave transmission/reception unit 24. At this time, the bridge member 31 is previously fixedly joined to the endoscope fitting member 18 by the screws 35.

When the bridge member 31 joined to the distal block is inserted into the tunnel-shaped path, the opposite ends of the ultrasonic wave transmission/reception unit 24 are respectively fixed, by adhesion, to the joining member 30 and the distal cap 19 which constitutes the distal block, and then, the joining member 30 and the bridge member 31 are fixedly joined to each other by the screws 33. In addition, the bridge member 31 to which the joining member 30 is fixedly joined is fixed to the distal ring 32 in the angle portion 2b by the screws 34. In this manner, the members constituting the ultrasonic observation unit are incorporated into the insertion portion 2.

The insertion portion 2 is assembled in the above-described manner. During the operation of the insertion portion 2 of the ultrasonic endoscope, if the angle portion 2b is bent when the insertion portion 2 is inserted into a body cavity or the like, the members inserted in the angle portion 2b tend to move. However, all the members inserted in the angle portion 2b have flexibility in the bending directions, and a bundle of the light guides 10b, the video cable 14 and the cable bundles 27B into which the cables 27 are grouped are deformable in their cross-sectional shapes, so that even if the above-described members are forced against other members during the bending operation of the angle portion 2b, there is no risk that disconnection, buckling, damage or the like occurs.

Figure 12A:
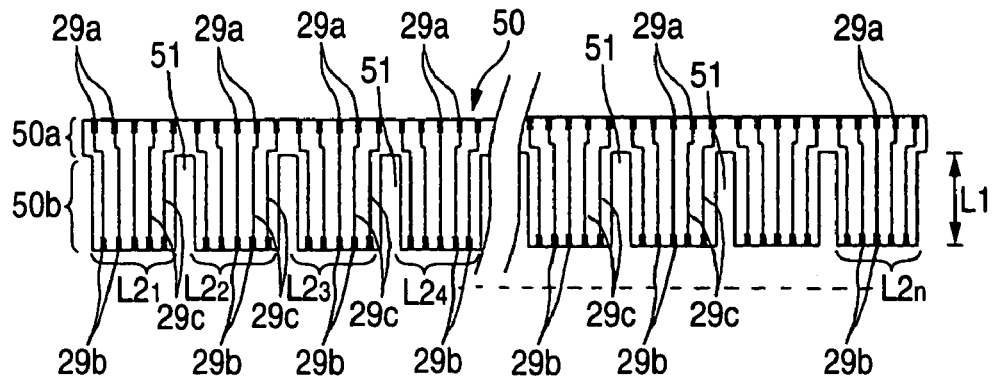
FIG. 12 is an explanatory view showing a process for forming a stepped cylindrical flexible circuit board from a planar resin film.

In addition, the flexible circuit board 28 may also be formed into a stepped cylindrical shape in advance. Patterns such as the terminal sections 29a and 29b and the wirings 29c are formed on the surface of the flexible circuit board 28. These patterns are desirably prepared by printing means. When the patterns are to be formed on the flexible circuit board 28 having the stepped cylindrical shape by printing means, as shown in FIG. 12A, a long resin film 50 is prepared, and the patterns made of the terminal sections 29a and 29b and the wirings 29c can be printed on the resin film 50 in a planar state.

Figure 12B:
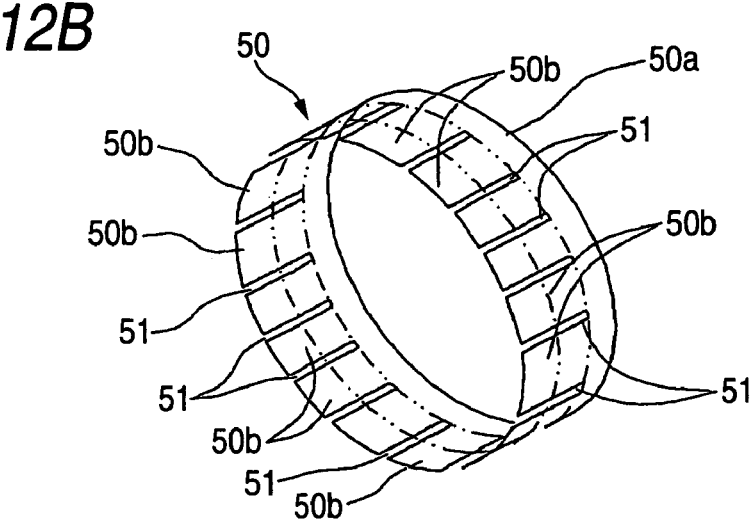
Figure 12C:
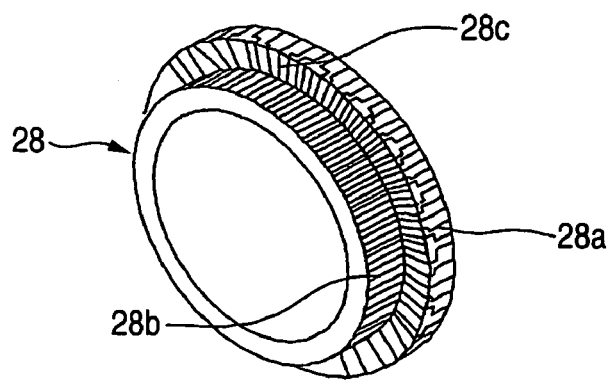

When the flexible circuit board 28 is formed into the stepped cylindrical shape, notches 51 each having a predetermined width are formed in the resin film 50 to a predetermined depth from one side thereof so that a continuous section 50a and discontinuous sections 50b arranged at a constant pitch are formed. Then, the resin film 50 is formed into a ring-like shape by bonding the opposite ends of the continuous section 50a to each other as shown in FIG. 12B. The obtained ring-shaped section forms the large-diameter section 28a of the flexible circuit board 28. Then, as shown by imaginary lines in FIG. 12B, the transition section from the continuous section 50a to the discontinuous sections 50b is folded inward at 90° and the intermediate position of the discontinuous sections 50b is folded back at 90°, so that the large-diameter section 28a and the small-diameter section 28b of the flexible circuit board 28 as well as the vertical section 28c which is the transition section between the large-diameter section 28a and the small-diameter section 28b are formed as shown in FIG. 12C. In addition, the small-diameter section 28b can be formed into a substantially continuous cylindrical shape by appropriately setting the width of each of the notches 51 and the number thereof.

In other words, as shown in FIG. 12B, the flexible circuit board 28 comprises: a long section (continuous section 50a) covering approximately the entire circumferential length of the large-diameter section; and a plurality of strip-shaped discontinuous sections 50b having a length ($L2_1+L2_2+L2_3+L2_4+ \ldots +L2_n$) approximately equal to a circumferential length of the small-diameter section Here, each of $L2_1$, $L2_2$, $L2_3$, $L2_4$, ... and $L2_n$ is a circumferential length of each of the strip-shaped discontinuous sections 50b. Each of the discontinuous sections 50b has a length L1 extending from: a transition section from the long section to the stepped section; to an end section of the support section.

Figure 13:
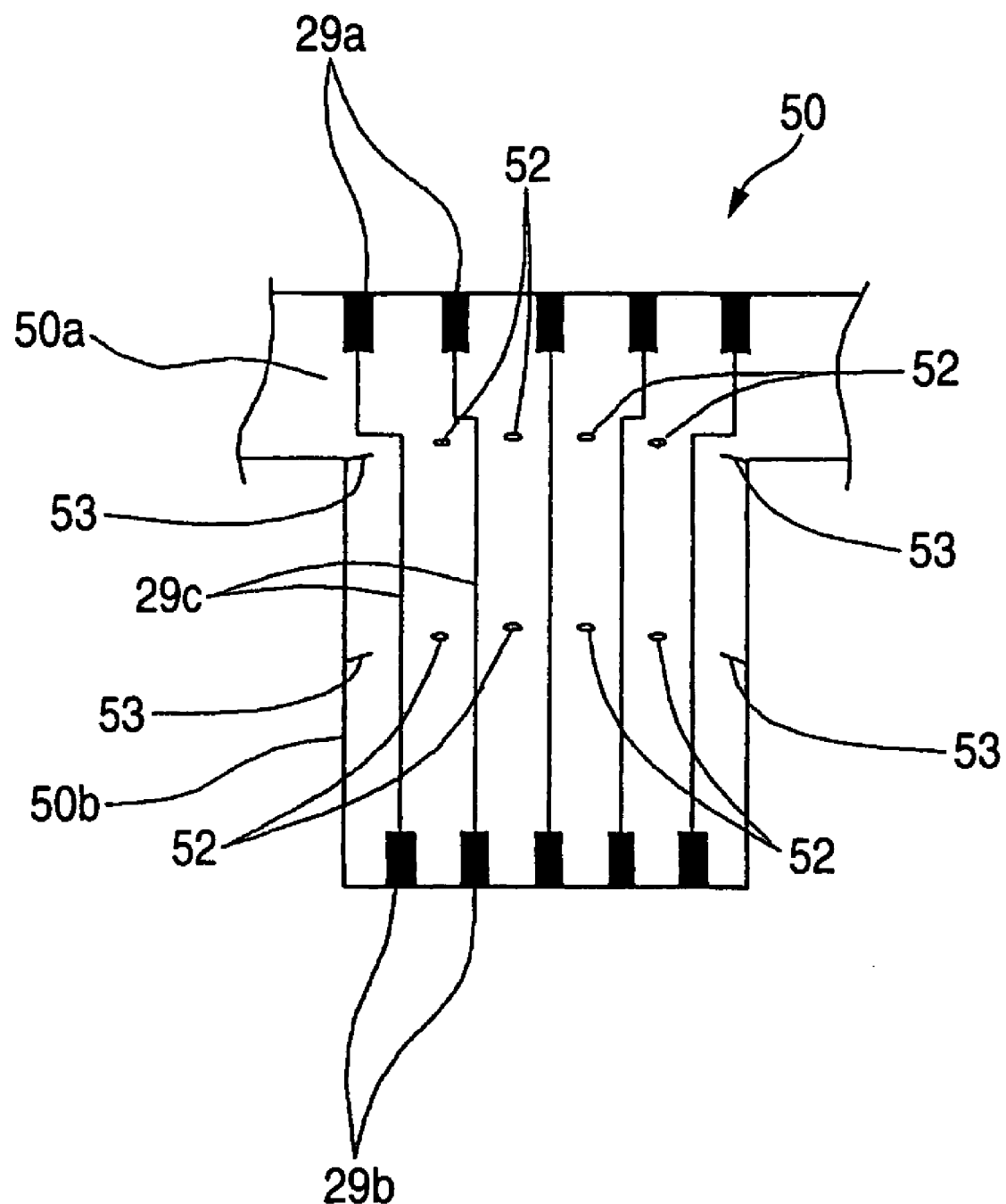
FIG. 13 is an enlarged front view showing the folding structure of a discontinuous section of the resin film.

The above-mentioned two folding sections must be folded not linearly but circularly. Accordingly, if either of the two folding sections is simply folded, stress is applied to a folded section, so that wrinkles or irregularities may be partially formed in the folded section. In order to prevent such problem and sharply fold both of the folding sections at 90°, as shown in FIG. 13, a predetermined number of small holes 52 may be formed along each folding line and cuts 53 may be formed in each of the discontinuous sections 50b at the opposite ends thereof. The small holes 52 and the cuts 53 serve a stress release function when the folding sections are circularly bent, so that the folding lines can be sharply finished. Accordingly, the strength with which the flexible circuit board 28 is stuck to the backing layer 22 is improved, and stress can be prevented from acting on the ultrasonic transducers 21 to which the flexible circuit board 28 is connected.

Figure 15:
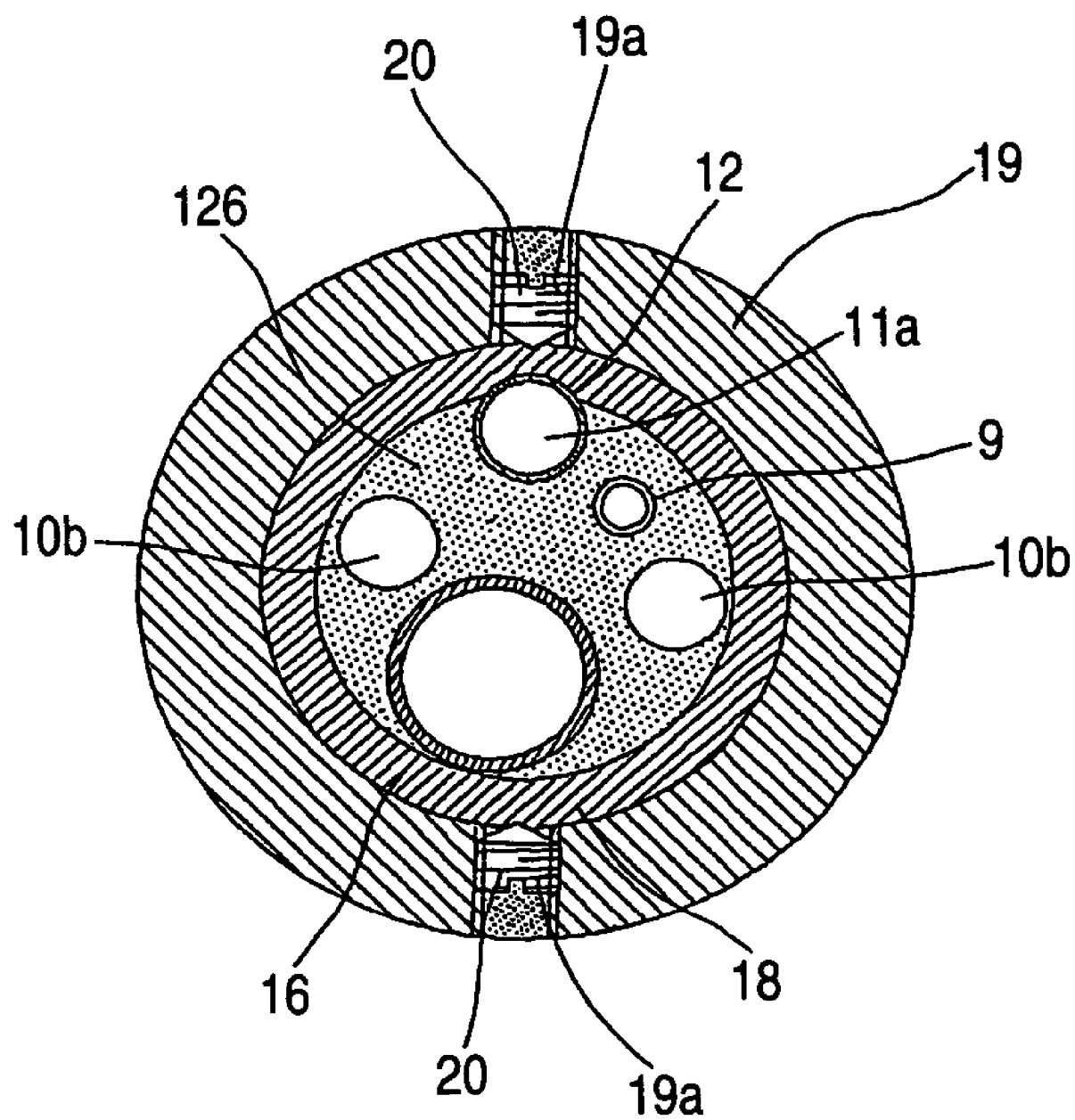
FIG. 15 is a cross-sectional view taken along line A'-A' of FIG. 14.
Figure 16:
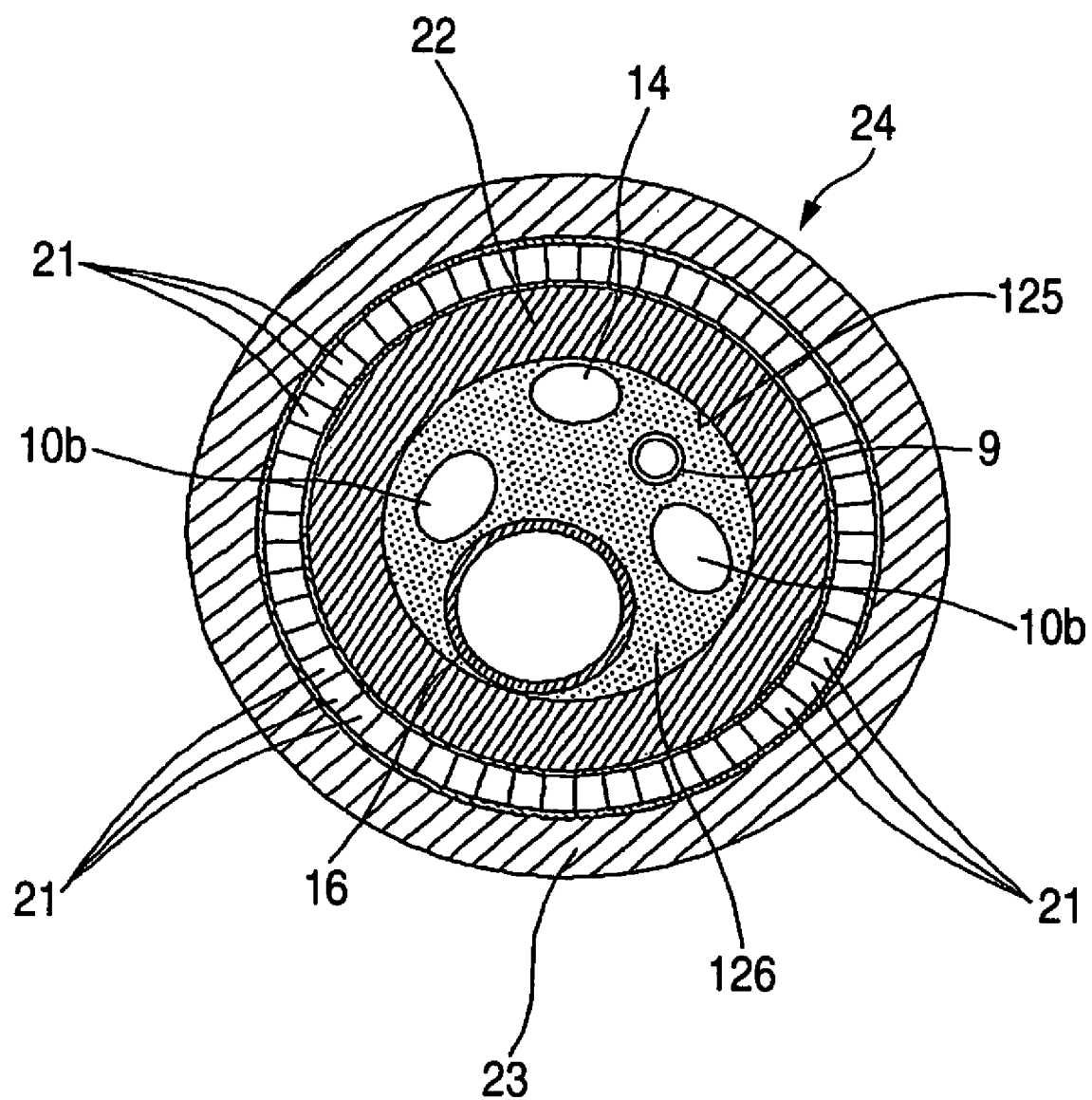
FIG. 16 is a cross-sectional view taken along line B'-B' of FIG. 14.

Another embodiment of the distal end of the insertion portion 2 will be described below with reference to FIGS. 14 to 16.

As described above, the ultrasonic wave transmission/reception unit 24 has an approximately cylindrical shape, and its inner circumferential surface forms a tunnel-shaped path 125. Accordingly, each of the members constituting the endoscopic mechanism is inserted into the tunnel-shaped path 125 which is formed by the inner circumferential surface of the backing layer 22 in the ultrasonic wave transmission/reception unit 24, and is extended from the ultrasonic wave transmission/reception unit 24 toward the distal end and is fixed to the endoscope fitting member 118 covered with the distal cap 19. A proximal end section of the endoscope fitting member 118 is formed as a large-diameter step 118a. A distal end section of the acoustic lens 23 which constitutes the ultrasonic wave transmission/reception unit 24 is extended to a position forward of the ultrasonic transducers 21 and is fitted on the large-diameter step 118a, and the ultrasonic wave transmission/reception unit 24 is fixed to the large-diameter step 118a by adhesion or the like. The proximal end of the ultrasonic wave transmission/reception unit 24 abut on a joining member 30 joined by screws 34 to a forward end ring 32a of an angle ring 32 which constitutes the structure of the angle portion 2b, and the proximal end and the joining member 30 are adhesively fixed to each other.

Figure 14:
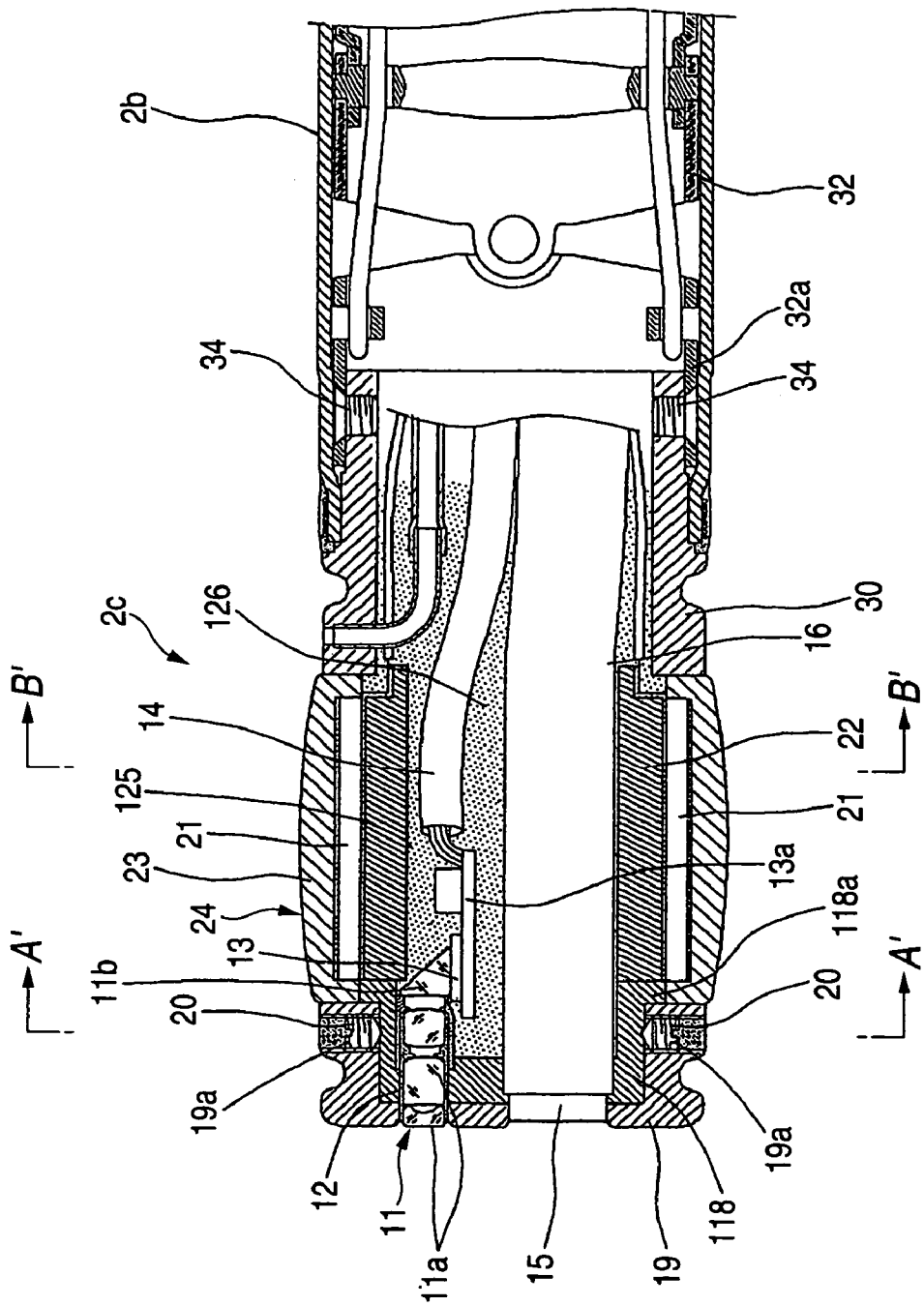
FIG. 14 is a vertical cross-sectional view of the distal hard portion.

Accordingly, as is apparent from FIG. 14, the narrowest section in the inside of the insertion portion 2 of the ultrasonic endoscope is a section in which the ultrasonic wave transmission/reception unit 24 is fitted, i.e., the section of the tunnel-shaped path 125 that is extended in the inside of the backing layer 22. As the endoscopic mechanism, the prism 11b which constitutes the observation section 11, the solid-state image pickup device 13 and the circuit board 13a thereof, and a distal end of the video signal cable 14 are positioned in the above-mentioned section. In addition, the light guides 10b (refer to FIGS. 15 and 16) which constitutes the illumination sections 10, the connection pipe 16 which constitutes a path through which a treatment equipment is to be inserted, and an air/water feed tube 9 are arranged in the inside of the backing layer 22. Accordingly, the size of the tunnel-shaped path 125 is restricted by the thickness of the backing layer 22. However, the size of the tunnel-shaped path 125 is set to a dimension enough to allow the above-mentioned endoscopic mechanism to be inserted through the tunnel-shaped path 125. If the outside diameter of the tunnel-shaped path 125 is set to a predetermined value, there is a case where the thickness of the backing layer 22 hinders the function thereof, i.e., the backing layer 22 cannot completely absorb echoes of ultrasonic waves transmitted from surfaces opposite to ultrasonic-wave transmission/reception surfaces.

Ultrasonic waves which travel from the ultrasonic transducers 21 toward the backing layer 22 are reflected at the interface between the backing layer 22 and an air layer. In addition, if a member different in acoustic impedance from the backing layer 22 abuts on the backing layer 22, echoes are also produced from the member.

For this reason, after each member constituting the endoscopic mechanism has been fitted in the inside of the tunnel-shaped path 125, a filler 126 made of the same material as the backing layer 22 is charged into the tunnel-shaped path 125 in a molten state. The filler 126 enters the space between each member constituting the endoscopic mechanism, in the inside of the backing layer 22. In addition, members which abut on or are close to the backing layer 22, such as the connection pipe 16 constituting a treatment equipment insertion path, can be displaced toward the center of the tunnel-shaped path 125.

The filler 126 made of the same material as the backing layer 22 is charged into the tunnel-shaped path 125 in the above-mentioned manner, so that the tunnel-shaped path 125 in which the backing layer 22 is formed is densely charged with the filler 126 so as to prevent substantial penetration of air.

According to the above-described construction, when ultrasonic pulses are transmitted from the ultrasonic transducers 21 which constitute the ultrasonic wave transmission/reception unit 24, ultrasonic waves traveling toward the backing layer 22 travel toward the inside of the filler 126 without being reflected at the inner surfaces of the backing layer 22. Accordingly, even if the thickness of the backing layer 22 is thin, reflections from the sides opposite to the transmission/reception surfaces of the respective ultrasonic transducers 21 do not occur.

The section in which the tunnel-shaped path 125 is provided is the distal hard portion 2c of the insertion portion 2. Accordingly, even if the filler 126 is charged into the section to fix the members inserted therein, special problems do not occur, and when impact or the like is applied to a distal end of the insertion portion 2, it is possible to protect the solid-state image pickup device 13 and the circuit board 13a thereof which constitute the observation section 11, as well as the video signal cable 14 extended from the circuit board 13a. Furthermore, it is possible to maintain the airtightness of the lens barrel 12.

The entire disclosure of each and every foreign patent application from which the benefit of foreign priority has been claimed in the present application is incorporated herein by reference, as if fully set forth.

What is claimed is:

1. An ultrasonic endoscope, comprising:
   an insertion portion comprising a distal hard portion including an endoscopic observation unit having at least an illumination section and an observation section at its distal end surface, and an electronic scanning type of ultrasonic observation unit fitted on an outer circumferential section of the endoscopic observation unit, wherein the ultrasonic observation unit includes
      an ultrasonic transducer array having a plurality of ultrasonic transducers arranged cylindrically or circularly, and a backing layer cylindrically formed on an inner circumferential surface of the ultrasonic transducer array; and
      a flexible circuit board, arranged between the ultrasonic transducer array and the backing layer, on which is formed a plurality of first terminals each directly connected to an electrode of a respective one of the ultrasonic transducers, a plurality of second terminals to which cables are respectively directly connected, and wiring patterns respectively formed between the first terminals and the second terminals to directly connect the first terminals and the second terminals,
   wherein the flexible circuit board has a stepped structure having a large-diameter section on which the first terminals are formed on an external surface side, a small-diameter section on which the second terminals are formed on an external surface side, and an annular support section formed on an inner circumferential side of the small-diameter section.

2. The ultrasonic endoscope according to claim 1,
   wherein the backing layer is projected by a predetermined length from an end section of the ultrasonic transducer array toward a proximal side of the distal hard portion, and
   an outer circumferential surface of a section projected by the predetermined length is reduced in diameter to form the stepped structure, the support section being formed by a reduced-diameter section of the stepped structure.

3. The ultrasonic endoscope according to claim 1,
   wherein the flexible circuit board comprises:
   a long section covering approximately the entire circumferential length of the large-diameter section; and
   a plurality of strip-shaped discontinuous sections having a first length approximately equal to a circumferential length of the small-diameter section,
   wherein each of the discontinuous sections has a second length extending from a transition section from the long section to the stepped section, to an end section of the support section.

4. The ultrasonic endoscope according to claim 3,
   wherein each of the discontinuous sections of the flexible circuit board is constructed so that at least either a plurality of small holes or a plurality of cuts are formed along folding lines in (i) a transition section from the large-diameter section to the stepped section, and (ii) a transition section from the stepped section to the small-diameter section.

5. The ultrasonic endoscope according to claim 1,
   wherein an endoscopic mechanism is inserted in an inside of a tunnel-shaped path formed in an inside of the backing layer, the endoscopic mechanism comprising:
   the endoscopic observation unit; and
   a treatment equipment insertion channel,
   wherein a filler which is a same as or close to the backing layer in acoustic impedance is charged in a spatial area which is produced in a section where the endoscopic mechanism is arranged in the inside of the backing layer.

6. The ultrasonic endoscope according to claim 5,
   wherein the filler comprises a same material as the backing layer and a solid-state image pickup device is provided in the observation section, at least part of the solid-state image pickup device being embedded in an inside of the filler.

* * * * *